United States Patent [19]
Gillespie et al.

[11] Patent Number: 5,633,397
[45] Date of Patent: May 27, 1997

[54] PREPARATION OF AMMONIUM GLYPHOSATE VIA A GAS-SOLID REACTION SYSTEM

[75] Inventors: Jane L. Gillespie, University City; Thomas M. Day, Creve Coeur; Richard M. Kramer, Chesterfield, all of Mo.

[73] Assignee: Monsanto Company, St. Louis, Mo.

[21] Appl. No.: 485,316

[22] Filed: Jun. 7, 1995

[51] Int. Cl.$^6$ .................................................. C07F 9/38
[52] U.S. Cl. ................................................ 562/17; 558/133
[58] Field of Search ............................ 558/133; 562/17

[56] References Cited

U.S. PATENT DOCUMENTS

| | | | |
|---|---|---|---|
| 3,671,612 | 6/1972 | Roszinski et al. | 260/987 |
| 5,047,079 | 9/1991 | Djafar et al. | 71/86 |
| 5,070,197 | 12/1991 | Chin et al. | 544/11 |
| 5,266,553 | 11/1993 | Champion | 504/206 |
| 5,324,708 | 6/1994 | Moreno | 504/206 |
| 5,410,075 | 4/1995 | Moreno et al. | 562/17 |

FOREIGN PATENT DOCUMENTS

| | | | |
|---|---|---|---|
| 0238240 | 9/1987 | European Pat. Off. | A01N 25/12 |
| 0256608 | 2/1988 | European Pat. Off. | A01N 25/14 |
| 0394211 | 4/1990 | European Pat. Off. | |
| 0582561 | 2/1994 | European Pat. Off. | A01N 57/20 |
| WO87/04595 | 8/1987 | WIPO. | |
| WO90/07275 | 7/1990 | WIPO. | |
| WO92/12637 | 8/1992 | WIPO. | |
| WO92/18513 | 10/1992 | WIPO | C07F 9/38 |
| WO94/10844 | 5/1994 | WIPO. | |

*Primary Examiner*—Gary Geist
*Assistant Examiner*—Barbara S. Frazier
*Attorney, Agent, or Firm*—Howell & Hafer-Kamp L.C.; Gordon F. Sieckmann; Arnold, White & Durkee

[57] ABSTRACT

Solid N-phosphonomethylglycine or glyphosate acid in "wet cake" form is charged to a suitable mixer/reactor. A stoichiometric equivalent of anhydrous ammonia gas is fed to the mixer for direct reaction with the glyphosate acid as it is agitated within the mixer. A water jacket containing circulating water or other suitable heat transfer facilitating means readily known to those in the art is adapted to the mixer and used to remove heat from the reactor produced by the exothermic reaction. The moisture content of the glyphosate wet cake, the design of the mixer including a preferred close tolerance relation between the inner walls of the reactor and its mixing impellers together with the relative location of the ammonia gas inlet in the mixer/reactor and maintenance of a reaction temperature of about 60° C. or below are all important process variables. The ammonium glyphosate thereby produced is a highly sorptive, water-soluble powder suitable for end use as a plant growth regulator or as a herbicide without further processing. Due to the highly sorptive character of the reaction product, however, it is particularly well-suited for further formulation to absorb/adsorb an exceptionally high level of adjuvants such as wetting agents, anti-foaming agents and, in particular, surfactants.

34 Claims, No Drawings

PREPARATION OF AMMONIUM GLYPHOSATE VIA A GAS-SOLID REACTION SYSTEM

BACKGROUND

1. Field of the Invention

This invention relates to a dry, non-clumping herbicidal composition together with a method for making the composition.

More particularly, the present invention relates to a method for making an ammonium glyphosate herbicide by directly reacting ammonia gas with glyphosate acid. The reaction product dissolves readily and completely in water and can be used to prepare highly-loaded, adjuvant-containing dry glyphosate compositions.

2. Description of the Related Art

N-phosphonomethylglycine [HOOCCH$_2$NH CH$_2$PO(OH)$_2$], which is commonly referred to as glyphosate acid or simply glyphosate, is well known in the art as a highly effective herbicide. It is also known that glyphosate, an organic acid, has relatively low solubility in water. Thus, glyphosate is typically formulated as a water-soluble salt, particularly as the mono-isopropylamine (IPA) salt to kill or control weeds or plants. Glyphosate is sold commercially as an aqueous concentrate in the form of its IPA salt by Monsanto Company of St. Louis, Mo. (U.S.A.) under the registered trademark Roundup®.

Various salts of glyphosate, methods for preparing salts of glyphosate, formulations of glyphosate and methods of use for killing and controlling weeds and plants are disclosed in U.S. Pat. Nos. 3,799,758 and 4,405,531 issued to John E. Franz on Mar. 26, 1974 and Sep. 20, 1983 respectively. Other U.S. Patents which disclose salts of glyphosate include U.S. Pat. No. 4,315,765 issued to George B. Large on Feb. 16, 1982, U.S. Pat. No. 4,507,250 issued to Izak Bakel on Mar. 26, 1985, U.S. Pat. No. 4,397,676 issued to Izak Bakel on Aug. 9, 1983, U.S. Pat. No. 4,481,026 issued to Michael P. Prisbylla on Nov. 6, 1984 and U.S. Pat. No. 4,140,513 issued to Erhard J. Prill on Feb. 20, 1979. All of the foregoing patents, in their entireties, are herein incorporated by reference.

Roundup® brand herbicide is sold as a water-soluble liquid concentrate. However, efforts have recently been made in the art to develop a water-soluble dry/solid glyphosate formulation which has the equivalent efficacy of Roundup®.

Conventional reasons underlying these efforts have been desired cost savings in connection with the packaging, shipment and storage of a solid formulation versus a liquid. As can be appreciated, aqueous concentrates include a significant amount of solvent that adds to the size and weight of packaging containers and increases costs associated with post-manufacture delivery of the product to market.

A less readily apparent benefit also resides in the advantage of making a water-soluble, dry glyphosate. Namely, a granular formulation is believed to provide superior handling characteristics (i.e. controlled spillage) and is expected to be substantially lighter and less awkward to transport (and often hand carry) thereby making the product better suited for use in remote geographic locations.

Making a granular glyphosate formulation, however, entails overcoming inherent disadvantages relating principally to the increased production cost and comparative complexity of compounding a solid product from a combination of gaseous and solid reactants rather than making a product in solution from the same reactants.

Several methods of making a solid water-soluble glyphosate salt-containing composition are known. For example, in U.S. Pat. No. 5,047,079 which issued on Sep. 10, 1991 to Djafar, there is disclosed a method for preparing a phytotoxic composition comprising admixing isopropylamine with a molten surfactant to form a matrix, the surfactant being a solid at ambient temperatures.

In U.S. Pat. No. 5,070,197 which issued on Dec. 3, 1991 to Chin, et. al. an extrusion method is disclosed in which a Bronsted acid, N-phosphonomethyl glycine for example, is intimately admixed with sodium hydroxide in an extruder to produce a granular extrudate having a residual moisture content of no greater than 10%. Another method involving the production of a dry sodium glyphosate composition, albeit not involving extrusion, is disclosed in PCT application Publication No. WO 87/04595.

In U.S. Pat. No. 5,266,553 which issued on Nov. 30, 1993 to Champion, et. al. there is disclosed a method for preparing a dry, water-soluble salt of bentazon or of an herbicide containing a carboxylic acid functionality which involves repeated treatments of the salt with a neutralizing base selected from the group consisting of ammonia, an alkylamine, a hydroxyalkylamine, an alkaline salt of an alkali metal and combinations thereof.

In French Patent Publication No. 2.692.439 which was filed on May 19, 1993 and is assigned to Productos Osa SACIFIA, there is generally described a phytotoxic preparation comprising the monoammonium salt of N-phosphonomethylglycine as a powder or granule in combination with a wetting agent, surfactant and/or a pulverulent additive. As exemplified in the reference, the monoammonium salt is derived from reacting glyphosate acid with ammonium carbonate.

U.S. Pat. No. 5,324,708 which issued on Jun. 28, 1994 to Moreno, et. al. discloses a composition and related methods for preparing and using a non-hygroscopic monoammonium glyphosate salt such as the mono-isopropylammonium salt of N-(phosphono-methyl)-glycine and the mono-isopropylammonium salt of (3-amino-3-carboxypropyl)-methane phosphonic acid in dry powder form [sic].

In PCT application Publication No. WO 94/10844, published on May 26, 1994, a dry glyphosate composition is disclosed in which N-phosphonomethyl glycine is admixed with, inter alia, an inorganic or organic, non-caustic base material such as diammonium phosphate or a basic guanidine salt such as guanidinium acetate.

EPO application Publication No. 0 394 211 which was published on Oct. 24, 1990, discloses an invention comprising a dry pesticidal composition and related methods of use and production. More particularly, the invention relates to the enhanced solubility of the composition as achieved by the addition of an effective amount of an organosilicone block copolymer or a fluorocarbon wetting agent.

In EPO application Publication No. WO 90/07275 which was published on Jul. 12, 1990, there is disclosed an invention by which granular, water-soluble glyphosate compositions are made as by admixing, pan granulation, drying, spraying and extrusion.

In PCT application Publication No. WO 92/12637, which was published on Aug. 6, 1992, there is disclosed an invention relating to a dry, water soluble glyphosate including a composition comprising substantially nonreacted glyphosate, an acid acceptor such as sodium acetate and a liquid or solid surfactant.

All of the foregoing patents and publications are herein incorporated by reference.

3

The art indicates that considerable effort has been directed toward formulating compositions and related methods for making and using dry glyphosates. However, none of the above-identified references disclose a direct and practical method for producing a dry, water-dispersible, water-soluble and appreciably non-hygroscopic ammonium glyphosate composition which is capable of absorbing/adsorbing an exceptionally high level of adjuvants by reacting solid N-phosphonomethylglycine with relatively inexpensive and plentiful ammonia gas.

Thus, a need unsatisfied by known technology exists within the art for the present invention which accomplishes these and other objectives.

SUMMARY OF THE INVENTION

The unresolved needs of the art are satisfied by the present invention which provides an ammonium glyphosate dry herbicide composition and novel method for its production whereby the disadvantages associated with known dry compositions and related methods, as discussed, are overcome through heretofore unknown and undisclosed limitations.

In accordance with the present invention glyphosate acid in "wet cake" form having a moisture content of up to approximately 20 wt. % (i.e. weight loss on drying or LOD) is charged to a suitable reactor system such as a conventional mixing apparatus. As the mixer agitates the wet cake, it is neutralized by a stoichiometric equivalent of anhydrous ammonia gas which is fed directly to the mixer for reaction with the wet cake.

Because the reaction is exothermic, it is desirable to employ a means for facilitating heat transfer from the reactor system such as a fitted water jacket about the mixer or other means conventionally known in the art in order to dissipate heat produced by the reaction and thereby partially control the temperature of the reaction. Additionally in this regard, the configuration of the mixer/reaction vessel and, particularly self-cleaning features and the placement of the ammonia gas inlet have proven to be important process variables. Also, the internal reactor temperature is monitored and controlled such that a temperature of about 60° C. is not exceeded.

Further, and in combination, the relative moisture content of the wet cake and the rate at which the ammonia gas is added to the reaction, among other things, have also been found to be factors that influence the manageability of the reaction mass. Thus, an important aspect of the present invention relates to the manner in which all of these variables are managed in order that the heat balance can be controlled and a desirable product thereby produced.

The ammonium glyphosate composition produced in accordance with the process of the present invention is in the form of a powder which is suitable for end use as a plant growth regulator and/or a herbicide.

Perhaps more importantly, however, the powdered reaction mass/product due to its highly sorptive character is capable of being further formulated to absorb/adsorb an exceptionally high level of adjuvants such as wetting agents, anti-foaming agents and, particularly, surfactants. Thus, when so formulated, a very useful and highly desirable adjuvant-loaded product is formed which is every bit as good and effective as comparable products obtained by prior art processes which require more expensive starting materials.

Optionally, the powdered reaction product or the adjuvant-loaded product may each be granulated to provide a free-flowing (i.e. non-caking), substantially dust-free and water soluble ammonium glyphosate herbicide and/or plant growth regulator.

Still further optional procedures may be carried out using the powdered reaction product. For example, the powder may be further ground and/or dried prefatory to packaging.

Significant advantages achieved by the present invention reside in its relative simplicity and comparatively low cost of the reactants. Furthermore, the process of the present invention is very efficient. That is, because the ammonia gas is reacted directly with the solid glyphosate acid to produce a powder, the significant problem of isolating the ammonium glyphosate in solid form from a solution is eliminated.

DETAILED DESCRIPTION OF THE INVENTION

The present invention relates to a novel method for reacting N-phosphonomethylglycine (glyphosate acid) with anhydrous ammonia gas to produce high quality ammonium glyphosate powder, a key raw material used in the production of granular and/or surfactant-loaded dry glphosate compositions.

Until now, an effective and practical method for producing dry ammonium glyphosate powder capable of being further formulated to absorb/adsorb an exceptionally high level of adjuvants by reacting glyphosate acid and ammonia gas has not been known.

Instead, various alternate and less advantageous methods have been developed by which ammonium glyphosate as well as alkali metal glyphosates such as sodium glyphosate have been made in dry, powder form. For example, sodium glyphosate has been produced by reacting glyphosate acid with sodium acetate or by extruding the acid with sodium hydroxide as described above in PCT application Publication No. WO 92/12637 and U.S. Pat. No. 5,070,197 respectively.

Sodium glyphosate granules and powders have, until now, provided a satisfactory dry glyphosate composition. However, when compared to ammonium glyphosate compositions, the sodium alkali metal is many orders more hygroscopic meaning it is not as resistant against ambient humidity. Thus, the sodium alkali metal glyphosate is considered more difficult and more expensive to process as a dry composition and, once formed as such, these compositions have a greater tendency to agglomerate which results in undesirable "caking" of the finished material.

Also, due to the relative molecular weights of ammonia and sodium, sodium glyphosate salt compositions have a lower concentration of the active glyphosate than their counterpart ammonium glyphosate salt compositions. In addition, the per pound cost of sodium cation is much more expensive than the cost of obtaining an equivalent amount of the ammonium cation. The comparative disadvantages of sodium glyphosate compositions are, thus, apparent.

As previously noted, certain solid/solid reaction methods are also known for making dry ammonium glyphosate. Reacting ammonium bicarbonate with glyphosate acid, for example, as described above in French Publication No. 2.692.439 is believed to yield a dry ammonium glyphosate composition.

The invention disclosed herein, however, constitutes an advance in the art of making dry ammonium glyphosate notwithstanding known methods utilizing ammonium bicarbonate.

For example, in practicing the present invention which involves reacting anhydrous ammonia gas with solid N-phosphono-methylglycine, it has been observed that the per pound cost of ammonium cation derived from ammonium bicarbonate is several times more expensive than the per pound cost of obtaining an equivalent amount of the same cation from ammonia gas.

In the large-scale commercial production of amonium glyphosate, a cost differential such as this might alone militate in favor of an effective method, such as that disclosed herein, for producing a solid ammonium glyphosate using anhydrous ammonia gas as the source of ammonium cation.

As used herein the terms "solid" and/or "dry" mean the physical state in which the formulation has a specific shape and Volume and resists deformation. The solid may take the form of pellets, flakes, granules, powder or the like. Further, it will be understood that the solid formulation may subsequently be dissolved in a suitable diluent, usually and preferably water, and applied to the locus where plant regulation or eradication is desired as by spraying or other conventional means.

From a technical perspective, very little is known about the use of ammonia gas in processes such as that disclosed herein. When this is considered in combination with the safe, cost-effective and technically simple ammonia gas process of the present invention the results obtained thereby are not to be expected.

The reaction of ammonia gas with glyphosate acid to produce ammonium glyphosate is, perhaps, the least expensive and most direct chemical approach possible. This is because the reaction involves the most fundamental reactants including plentiful and comparatively inexpensive ammonia gas which is reacted with glyphosate acid in a simple addition reaction. Moreover, because the chemistry of the reaction is so simple, no by-products such as water are produced which would complicate the reaction and require removal such as is the case where ammonium hydroxide is reacted with glyphosate acid. Despite the obvious advantages of the process of the present invention, however, it has been observed that the reaction that occurs between N-phosphonomethylglycine and anhydrous ammonia gas is, typically, highly exothermic. Thus, in practicing the present invention, a major factor to be contended with relates to heat transfer away from the reaction vessel. Where the heat transfer in the reaction system is low and unmanaged, the reaction product thereby formed is often an undesirable "dough-like" cohesive mass and/or "glassy" solid reaction mass which may make it difficult to continue the reaction. Furthermore, such a product is not suitable for use as a finished product and is incompatible with conventional formulation equipment used in further processing.

Because heat transfer plays such an important role in the reaction of ammonia gas with glyphosate acid, it is very important that the reactor vessel in which the reaction takes place is designed in such a way as to ensure a high degree of unencumbered heat transfer away from the reactor.

In this regard, it is very desirable that the mixing apparatus/reactor have desirably close tolerances between the edges of the mixing components (i.e. impellers) and the internal walls of the reactor. This is because, as the reaction proceeds, there is a tendency for reaction mass/product to adhere to the interior walls of the reation vessel. Where the tolerances between the impellers and the walls is not sufficiently close as to permit the impellers to continuously scrape the product from the walls, the reaction mass/product forms a glassy solid lining along the inner walls of the reactor.

Even when such glassy product is formed in only a thin layer along the reactor walls, it can act as an insulating thermal barrier inside the reactor which reduces heat transfer and frustrates the role of heat transfer equipment already in place.

This condition and the glassy solid product formed in connection therewith are wholly distinct from the process of the present invention which allows for the formation of a highly desirable free-flowing powdered product which is particularly well-suited to be further formulated.

Thus, adherence to the novel process herein disclosed and the manner and extent to which the reaction between the glyphosate acid and the anhydrous ammonia gas is controlled in accordance with the process, are very significant in ensuring the creation of a solid, free-flowing (i.e.non-caking) and water soluble/dispersible ammonium glyphosate product which is characteristic of the present invention.

In accordance with the process of the present invention, the reactants are combined in such a manner as to ensure substantially uniform dispersion of the ammonia gas within the glyphosate wet cake. The temperature of the reaction is carefully monitored and controlled by various process variables including the rate of ammonia gas addition and by employing suitable heat transfer means widely known to those skilled in the art such as by adapting a circulating water jacket about the reactor and/or the reactor impellers in order that a free-flowing, readily handleable powdered product is generated. Adherence to the process of the present invention not only permits processing in conventional equipment or slightly modified versions thereof but also produces an ammonium glyphosate powder that can be used to make dry glyphosate products highly-loaded with adjuvants.

The inventors have determined that, among other things, the relative moisture content in the glyphosate acid starting material is an important aspect of the invention.

The amount of ammonia gas required in order to practice the invention is equivalent to that amount which is required to achieve approximately 95–105% neutralization of the acid which can be determined by conventional analytical methods readily known to those skilled in the art such as by pH measurement.

In accordance with the process of the present invention an amount of glyphosate acid wet cake having a moisture content of up to about 12 wt. % and not less than about 3 wt. % is charged to a suitable reactor system such as a conventional blender or mixer and preferably one having internal blending or mixing impellers designed in close tolerance to the internal walls of the reactor/mixer. A glyphosate composition having a higher moisture content may also be used in the process of the invention although it is preferred that such a composition first be dried to reduce the moisture content to within the preferred range.

Optionally, a pre-determined quantity of sodium sulfite may be added to the glyphosate acid to prevent the possible formation of nitrosamines. Although the addition of sodium sulfite is not necesssary to practice the invention and does not affect the reaction between the glyphosate acid and the ammonia gas, certain governmental regulations require that nitrosamine levels in agricultural products of this nature be below 1 ppm. Experience has shown that, when added, the effective range of sodium sulfite to be added as ensurance against the presence of unacceptable levels of nitrosamines is between about 0.2 and about 1.0 wt. % of the dried, finished product.

Once the glyphosate wet cake and sodium sulfite, optionally, have been charged to the reactor/mixer, one stoichiometric equivalent of anhydrous ammonia gas is then fed directly to the reactor while the wet cake is being agitated and blended. Because the reaction is exothermic, suitable heat transfer means such as a circulating cold water jacket or other means readily known to those skilled in the art should be adapted to the reactor system in order to facilitate heat transfer and thereby provide some control over the temperature of the reaction within the reactor.

Throughout the step of ammonia gas addition various process variables, including ammonia gas addition rate and reaction temperature, are controlled such that a free-flowing, readily handleable and highly sorptive powdery ammonium glyphosate product is formed.

As can be appreciated, the novel process can be readily practiced using conventional equipment which is preferably designed to be substantially self-cleaning. Also, however, other equipment not so designed may also be employed in which case some measure, such as perhaps intermittent manual scraping for example, must be incorporated in conjunction with the process in order to keep the heat transfer surfaces of the reactor clean and free from product build-up. Unless this measure is provided for, the reaction mass/product, with continued processing, forms a thermal insulating layer on the inner walls of the reactor which frustrates heat transfer and which may lead to an uncontrolled reaction temperature resulting in overheating of the product and thereby destroying its desirable characteristics.

The inventors have discovered that the manner in which the ammonia gas is introduced to the blender for reaction with the glyphosate acid is a very significant aspect of the invention. In accordance with the invention, the ammonia gas should be introduced to the reactor in such a manner as to ensure substantially thorough and uniform dispersion of the gas with the glyphosate acid. This precept is carried out in the invention when the inlet port or ports through which the ammonia gas is introduced into the reactor is/are positioned in such a manner as to ensure that sufficient quantities of the acid are being contacted with the gas, as the acid is being agitated and the gas is being introduced, to form a reaction mass/product which is the result of a reaction in which ammonia gas has been uniformly reacted with the glyphosate acid. The improper placement of the ammonia gas inlet(s) will likely result in fouling of the inlet(s) and/or the formation of an undesirable "dough-like" cohesive mass or solid glassy product. For example, where an inlet only permits the ammonia gas to react with a small, localized quantity of the glyphosate acid within the reactor, it is likely that a "hot spot" will be formed whereby the localized reaction mass overheats due to the build-up of excessive localized heat from the exothermic reaction. This phenomenon could not only contaminate the entire product being produced at the time, but also possibly clog the gas inlet(s) thereby raising the possibility of physical damage to the processing equipment and creating the possibility of an ammonia gas escape.

In addition to the other process variables identified, it has been determined that the temperature of the reaction mass is, at least partially, a function of the rate of ammonia gas addition to the reaction. In this regard it has been determined that it is desirable to maintain a reaction mass temperature of about 60° C. or less in order to maximize the production of a valuable product.

Under the process conditions disclosed and described, the direct reaction of ammonia gas with glyphosate acid results in the production of a highly desirable ammonium glyphosate product capable of being further formulated to absorb/adsorb an exceptionally high level of adjuvants. These conditions which include the configuration of the mixer/reactor, the relative moisture content of the starting glyphosate acid, the rate and manner in which ammonia gas is added to the reaction and various methods for facilitating heat transfer away from the reactor vessel are all designed to control the temperature of the reaction mass which, in turn, assures that a manageable powdered product suitable for further processing is obtained.

A number of process variables falling outside the scope of the requirements of the present invention will adversely affect the advantages achieved by the process of the present invention. For example, if the temperature in the reaction mass is allowed to rise above about 60° C., the quality of the reaction mass/product can be substantially deteriorated.

The following example illustrates production of the composition of the invention in accordance with the process described herein. All percentages are based upon weight, unless otherwise clearly indicated.

EXAMPLE 1

In a plant-scale reactor system comprised of a 300 Liter stainless steel horizontally mixer/reactor fitted with cross-flow mixing tools, a high-speed chopper and a water jacket containing circulating cold water, 94.6 lbs. of standard grade N-phosphonomethylglycine "wet cake" having an assayed moisture content of about 7.4 wt. % was charged to the mixer/reactor where it was immediately mixed.

Once all of the wet cake was deposited in the mixer, 0.4 lbs. of solid anhydrous sodium sulfite was also charged, optionally, to the mixer and admixed with the wet cake.

The admixture of wet cake and sodium sulfite was then circulated within the mixer/reactor for a time sufficient to obtain a substantially uniform mixture.

Through an inlet disposed centrally within the mixer/reactor whereat the largest volume of the admixture could be contacted, 8.65 lbs of anhydrous ammonia gas was then introduced into the reactor at a rate of about 0.2 lbs./min. and reacted directly with the glyphosate acid admixture. A temperature probe was positioned within the reactor in order to monitor the temperature of the exothermic acid-base reaction that ensued. A reaction mass temperature not exceeding 60° C. was maintained in part due to the rate of ammonia gas addition established in connection therewith.

Once the final product was obtained, it was dried in a vacuum oven at 50° C. under vacuum. The dried product was then ground in a hammer mill fitted with a 40 mesh screen. The resulting finished product exhibited a moisture content of no greater than 1.0 wt. %.

From the original reactants which included 94.6 lbs. of glyphosate acid (i.e. "wet cake" containing 7.4% LOD) and 8.65 lbs. of anhydrous ammonia gas, a theoretical product yield of 97 lbs. of dry, powdered ammonium glyphosate having a residual moisture content of approximately 1.0 wt. % can be obtained.

The product obtained in connection with the foregoing example has demonstrated excellent storage and stability characteristics. In fact when stored properly, as for example in sealed polyethylene bags, the product has proven not to degrade or cake after six months of actual warehousing.

As discussed in some detail above, the powdered reaction mass/product produced in accordance with the novel process of this invention is particularly well adapted to be further formulated to absorb/adsorb high levels of adjuvants.

In combination, the relative simplicity of the present invention, its ability to be practiced in conventional or slightly modified conventional equipment and the comparatively low cost of the ammonium cation furnished by the ammonia gas deem very significant the capacity of the powdered reaction mass/product to absorb/adsorb high levels of adjuvants.

While the choice of a particular adjuvant or combination of adjuvants will be easily made by those ordinarily skilled in the art without undue experimentation, Example 2 presented below illustrates the exceptional sorptive capacity of the powdered reaction mass/product when loaded with surfactant.

EXAMPLE 2

The powdered reaction mass/product formed by the process as illustrated in Example 1 can be used to make a dry formulation of ammonium glyphosate containing a high level of surfactant of at least up to about 20 wt. %.

To make such a highly loaded product, 16 kilograms of the powdered reaction mass/product is blended with 4 kilograms of a polyoxyethylene alkylamine surfactant and 1.4 kilograms of water in a jacketed batch kneader, such as a Fuji Paudal, for approximately 10 minutes with water at a temperature of about 80° C. circulating in the jacket. The dough that is formed is then extruded, as for example in a Fuji Paudal twin scre extruder, fitted with screens having approximatley 1 mm. diameter borings. The extrudate obtained consisted of discrete, "spaghetti-like" short noodles which did not stick together and which were easily and conveniently dried, such as for example in a Fitz-Aire fluid bed dryer, without formation of undesirable lumping.

The dry ammonium glyphosate herbicide of this invention is effective when subsequently dissolved or dispersed in a suitable diluent, preferably water, and applied to the locus of the target plant by spraying or other conventional means.

What is claimed is:

1. A method for preparing a phytoactive ammonium glyphosate comprising introducing anhydrous ammonia gas to a glyphosate acid medium to cause a reaction therebetween in a manner such that said gas is uniformly dispersed with said acid and such that the transfer of heat away from said reaction is controlled to produce a free-flowing, powdered product.

2. The method of claim 1 wherein said glyphosate acid has a moisture content of up to approximately 12 wt %.

3. The method of claim 1 wherein said glyphosate acid may have a moisture content of up to approximately 20 wt. % but, in such case, is first dried to reduce said moisture content to up to about 12 wt. % prior to being reacted with said ammonia gas.

4. The method of claim 1 wherein said glyphosate acid has a moisture content of no less than approximately 3 wt. %.

5. The method of claim 1 wherein said glyphosate acid has a moisture content of up to approximately 12 wt. % but not less than approximately 3 wt. %.

6. The method of claim 1 wherein said reaction is carried out in a substantially self-cleaning conventional mixer.

7. The method of claim 1 wherein the temperature of the reaction mass/product generated by said reaction is maintained at approximately 60° C. and controlled, at least in part, by adjusting the rate at which said ammonia gas is reacted with said acid.

8. The method of claim 1 wherein said reaction is carried out in a substantially self-cleaning mixer/reactor and wherein the temperature of the reaction mass/product generated by said reaction is maintained at approximately 60° C. and controlled, at least in part, by ensuring that the interior walls of said reactor are free from product build-up.

9. The method of claim 1 wherein said reaction is carried out in a substantially self-cleaning mixer/reactor and wherein the temperature of the reaction mass/product generated by said reaction is maintained at approximately 60° C. and controlled, at least in part, by a combination of two or more process variables which include adapting a circulating water jacket or other conventionally known means for facilitating heat transfer to said mixer/reactor, adjusting the rate at which said ammonia gas is reacted with said acid to maintain said temperature and ensuring that the interior walls of said reactor are free from product build-up.

10. The method of claim 1 wherein said ammonia gas and said acid are reacted in substantially equivalent stoichiometric amounts.

11. The method of claim 1 wherein the required amount of said ammonia gas is equivalent to an amount sufficient to neutralize approximately 95 to about 105% of said acid.

12. The method of claim 6 wherein said glyphosate acid has a moisture content of up to approximately 12 wt. % but not less than approximately 3 wt. % and wherein the temperature of the reaction mass/product generated by said reaction is maintained at approximately 60° C. and controlled, at least in part, by adjusting the rate at which said ammonia gas is reacted with said acid.

13. The method of claim 6 wherein said glyphosate acid has a moisture content of up to approximately 12 wt. % but not less than approximately 3 wt. % and wherein the temperature of the reaction mass/product generated by said reaction is maintained at approximately 60° C. and controlled, at least in part, by ensuring that the interior walls of said reactor are free from product build-up.

14. The method of claim 9 wherein said combination of process variables further includes adapting to said mixer/reactor a circulating water jacket or other conventionally known means for facilitating heat transfer.

15. A method for preparing a dry ammonium glyphosate capable of being highly loaded with adjuvants Comprising the steps of:
    (a) charging to a substantially self-cleaning mixer/reactor a quantity of glyphosate acid wet cake;
    (b) introducing a quantity of anhydrous ammonia gas to said reactor to cause a reaction between said gas and said acid; and
    (c) controlling the temperature of the reaction mass/product generated by said reaction in a manner such as to maintain said temperature at a desired level of up to about 60° C.

16. The method of claim 15 wherein said glyphosate acid wet cake has a moisture content of at least about 3 wt. % and up to about 12 wt. % and wherein said gas and said acid are reacted in substantially equivalent stoichiometric amounts.

17. The method of claim 15 wherein the step of controlling said temperature of said reaction mass/product further includes adjusting the rate at which said ammonia gas is introduced to maintain said temperature at said desired level.

18. The method of claim 15 wherein the step of controlling said temperature of said reaction mass/product further includes adapting a circulating water jacket or other conventionally known means for facilitating heat transfer to said mixer/reactor.

19. The method of claim 15 wherein the step of controlling said temperature of said reaction mass/product further includes, in any combination of two or more, adapting a circulating water jacket or other conventionally known means for facilitating heat transfer to said blender/reactor, adjusting the rate at which said ammonia gas is introduced to maintain said temperature at said desired level and/or by ensuring that the interior walls of said reactor are free from product build-up.

20. The method of claim 15 wherein the step of introducing said ammonia gas further includes means for ensuring that said gas is uniformly dispersed with said acid at the time of said reaction.

21. A method for preparing a phytoactive ammonium glyphosate comprising introducing anhydrous ammonia gas to a glyphosate acid medium to cause a reaction therebetween in a manner such that said gas is uniformly dispersed with said acid and such that heat is transferred away from said reaction so that the temperature of the reaction mass/product generated by said reaction is maintained at a temperature not exceeding approximately 60°.

22. The method of claim 21 wherein said glyphosate acid has a moisture content of up to approximately 12 wt. %.

23. The method of claim 21 wherein said glyphosate acid may have a moisture content of up to approximately 20 wt. % but, in such case, is first dried to reduce said moisture content to up to about 12 wt. % prior to being reacted with said ammonia gas.

24. The method of claim 21 wherein said glyphosate acid has a moisture content of no less than approximately 3 wt. %.

25. The method of claim 21 wherein said glyphosate acid has a moisture content of up to approximately 12 wt. % but not less than approximately 3 wt. %.

26. The method of claim 21 wherein said reaction is carried out in a substantially self-cleaning conventional mixer.

27. The method of claim 21 wherein the temperature of the reaction mass/product generated by said reaction is maintained at approximately 60° C. and controlled, at least in part, by adjusting the rate at which said ammonia gas is reacted with said acid.

28. The method of claim 21 wherein said reaction is carried out in a substantially self-cleaning mixer/reactor and wherein the temperature of the reaction mass/product generated by said reaction is maintained at approximately 60° C. and controlled, at least in part, by ensuring that the interior walls of said reactor are free from product build-up.

29. The method of claim 21 wherein said reaction is carried out in a substantially self-cleaning mixer/reactor and wherein the temperature of the reaction mass/product generated by said reaction is maintained at approximately 60° C. and controlled, at least in part, by a combination of two or more process variables which include adapting a circulating water jacket or other conventionally known means for facilitating heat transfer to said mixer/reactor, adjusting the rate at which said ammonia gas is reacted with said acid to maintain said temperature and ensuring that the interior walls of said reactor are free from product build-up.

30. The method of claim 21 wherein said ammonia gas and said acid are reacted in substantially equivalent stoichiometric amounts.

31. The method of claim 21 wherein the required amount of said ammonia gas is equivalent to an amount sufficient to neutralize approximately 95 to about 105% of said acid.

32. The method of claim 26 wherein said glyphosate acid has a moisture content of up to approximately 12 wt. % but not less than approximately 3 wt. % and wherein the temperature of the reaction mass/product generated by said reaction is maintained at approximately 60° C. and controlled, at least in part, by adjusting the rate at which said ammonia gas is reacted with said acid.

33. The method of claim 26 wherein said glyphosate acid has a moisture content of up to approximately 12 wt. % but not less than approximately 3 wt. % and wherein the temperature of the reaction mass/product generated by said reaction is maintained at approximately 60° C. and controlled, at least in part, by ensuring that the interior walls of said reactor are free from product build-up.

34. The method of claim 29 wherein said combination of process variables further includes adapting to said mixer/reactor a circulating water Jacket or other conventionally known means for facilitating heat transfer.

* * * * *